US00PP28775P2

(12) United States Plant Patent
Hamilton et al.

(10) Patent No.: US PP28,775 P2
(45) Date of Patent: Dec. 19, 2017

(54) RASPBERRY PLANT VARIETY NAMED 'DRISRASPTEN'

(50) Latin Name: ***Rubus idaeus* L.**
Varietal Denomination: DrisRaspTen

(71) Applicant: Driscoll's, Inc., Watsonville, CA (US)

(72) Inventors: Brian K. Hamilton, Richmond, TX (US); Carlos D. Fear, Aptos, CA (US); Matthias D. Vitten, Aptos, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 14/999,878

(22) Filed: Jul. 13, 2016

(51) Int. Cl.
*A01H 5/08* (2006.01)

(52) U.S. Cl.
USPC ..... Plt./204

(58) Field of Classification Search
USPC ..... Plt./204
See application file for complete search history.

(56) References Cited

U.S. PATENT DOCUMENTS

| | | | |
|---|---|---|---|
| PP4,486 | P | 11/1979 | Reiter |
| PP6,493 | P | 12/1988 | Wilhelm |
| PP7,436 | P | 2/1991 | Ackerman |
| PP7,437 | P | 2/1991 | Ackerman |
| PP8,022 | P | 11/1992 | Wilhelm |
| PP8,027 | P | 11/1992 | Wilhelm |
| PP9,340 | P | 10/1995 | Wilhelm et al. |
| PP9,653 | P | 10/1996 | Wilhelm et al. |
| PP9,696 | P | 11/1996 | Fear |
| PP11,067 | P | 9/1999 | Fear et al. |
| PP11,087 | P | 10/1999 | Fear et al. |
| PP11,094 | P | 10/1999 | Fear et al. |
| PP11,102 | P | 10/1999 | Fear et al. |
| PP14,761 | P2 | 5/2004 | Fear et al. |
| PP14,781 | P2 | 5/2004 | Fear et al. |
| PP14,804 | P2 | 5/2004 | Fear et al. |
| PP14,860 | P2 | 6/2004 | Fear et al. |
| PP14,903 | P2 | 6/2004 | Fear et al. |
| PP14,904 | P2 | 6/2004 | Fear et al. |
| PP18,658 | P3 | 3/2008 | Fear et al. |
| PP18,659 | P3 | 3/2008 | Fear et al. |
| PP19,137 | P3 | 8/2008 | Harrison et al. |
| PP19,656 | P2 | 1/2009 | Hamilton et al. |
| PP22,246 | P3 | 11/2011 | Hamilton et al. |
| PP22,731 | P2 | 5/2012 | Fear et al. |
| PP23,477 | P3 | 3/2013 | Hamilton et al. |
| PP24,610 | P3 | 7/2014 | Hamilton et al. |
| PP25,044 | P3 | 11/2014 | Hamilton et al. |
| PP25,045 | P3 | 11/2014 | Hamilton et al. |
| 2016/0219774 | P1 | 7/2016 | Hamilton et al. |

OTHER PUBLICATIONS

Vitten et al., "U.S. Appl. No. 14/999,293, filed Apr. 21, 2016, titled Raspberry Plant Named DrisRaspNine".
Cousineau et al. "Use of Isoenzyme Analysis to Characterize Raspberry Cultivars and Detect Cultivar Mislabeling", HortScience vol. 27, No. 9, 1992, pp. 1023-1025.
Williams et al. "DNA Polymorphisms Amplified by Arbitrary Primers are Useful. As Genetic Markers", Nucleic Acids Research,vol. 18, No. 22, 1990, pp. 6531-6535.

*Primary Examiner* — Annette H Para
(74) *Attorney, Agent, or Firm* — Morrison & Foerster LLP

(57) ABSTRACT

A new and distinct variety of raspberry plant named 'DrisRaspTen', particularly distinguished by producing multicolored fruit, a low number of young shoots, anthocyanin pigmentation present in canes and prickles, large fruit size, low seed weight, and a high length to width ratio is disclosed.

2 Drawing Sheets

Latin name: Botanical classification: *Rubus idaeus* L.

Varietal denomination: The varietal denomination of the claimed variety of raspberry plant is 'DrisRaspTen'.

BACKGROUND OF THE INVENTION

Raspberries are the edible fruit of a multitude of plant species in the genus *Rubus* of the rose family. Most raspberry species are in the subgenus Idaeobatus. Raspberry plants are perennial plants with woody stems. Many of the most important modern commercial red raspberry cultivars derive from hybrids between *R. idaeus* and *R. strigosus*. Recent breeding has resulted in cultivars that are thornless and more strongly upright, not needing staking.

Both the red and the black raspberry species have albino-like pale-yellow natural or horticultural variants. Fruits from such plants are called golden raspberries or yellow raspberries. Most pale-fruited raspberries commercially sold in the eastern United States are derivatives of red raspberries. Yellow-fruited variants of the black raspberry are sometimes grown in home gardens. Despite their dissimilar appearance, golden raspberries retain the distinctive flavor of their respective red or black species.

An individual raspberry fruit is made up of around 100 drupelets, each of which contains a juicy pulp and a single central seed. A raspberry bush can yield several hundred berries a year. Unlike blackberries and dewberries, a raspberry has a hollow core once it is removed from the receptacle.

Raspberries are traditionally planted in the winter as dormant canes, but planting plugs produced by tissue culture is also common. Additionally, the long cane production method consists of growing canes for 1 year in cold climates where the bud break is early, and then transplanting the canes to warm climates where they quickly flower and can produce an early season crop. A very vigorous crop, raspberries spread well and can be considered invasive, using extended underground shoots (also known as suckers or basal shoots) that can develop roots and individual plants.

Raspberries are a popular fruit that are recognized for their antioxidants, high fiber, and as a good source of vitamin C. Raspberry fruit is typically consumed as fresh fruit, individually quick frozen (IQF) fruit, or in prepared foods, such as purées, juices, jellies, jams, grocery items, baked goods, and snack foods.

Raspberry is an important and valuable commercial fruit crop, widely grown in all temperate regions of the world. Accordingly, there is a need for new varieties of raspberry plant. In particular, there is a need for improved varieties of raspberry plant that are stable, high yielding, and agronomically sound.

SUMMARY OF THE INVENTION

In order to meet these needs, the present invention is directed to an improved variety of raspberry plant. In particular, the invention relates to a new and distinct variety of raspberry plant (*Rubus idaeus* L), which has been denominated as 'DrisRaspTen', and more particularly to a raspberry plant that produces fruit having a multicolored phenotype. As described herein with relation to fruit produced by 'DrisRaspTen', multicolor phenotype refers to a color variation of the fruit that typically ranges from red to yellow within a raspberry drupelet. In some embodiments, the red color may be accentuated by sun exposure. In some embodiments, the red color may be more prominent at the base of the style and the yellow color may be more prominent away from the style. In some embodiments, fruit produced by 'DrisRaspTen' is exposed to sunshine to express the multicolor phenotype. In some embodiments, low cane emergence improves tissue culture propagation of 'DrisRaspTen'.

Raspberry plant variety 'DrisRaspTen' was discovered in Santa Cruz County, Calif. in August of Year 1 and originated from a controlled pollination cross between the proprietary female parent raspberry plant 'Driscoll Estrella' (U.S. Plant Pat. No. 19,137) and the proprietary male parent raspberry plant 'Driscoll Maravilla' (U.S. Plant Pat. No. 14,804). The original seedling of the new variety was first asexually propagated by tissue culture at a nursery in Santa Cruz County, Calif. 'DrisRaspTen' was subsequently asexually propagated over several generations through cycles of tissue culture multiplication and subsequent growth, and underwent further testing in Santa Cruz County, Calif. for six years. The present invention has been found to be stable and reproduce true to type through successive asexual propagations via tissue culture and root cuttings.

'DrisRaspTen' exhibits the following distinguishing characteristics when grown under normal horticultural practices in Santa Cruz County, Calif.:

1. Produces multicolored fruit;
2. Low number of young shoots;
3. Anthocyanin pigmentation present in canes and prickles;
4. Large fruit size;
5. High fruit firmness;
6. Low seed weight;
7. High length to width ratio;
8. Pleasant fruit flavor;
9. Good yield;
10. Vigorous growth.

BRIEF DESCRIPTION OF THE DRAWINGS

This new raspberry plant is illustrated by the accompanying photographs, which show fruit of the plant, as well as the primocanes, flowers, and leaves. The colors shown are as true as can be reasonably obtained by conventional photographic procedures. The photographs are of plants that are six months old.

DETAILED BOTANICAL DESCRIPTION

Figures 1A, 1B:
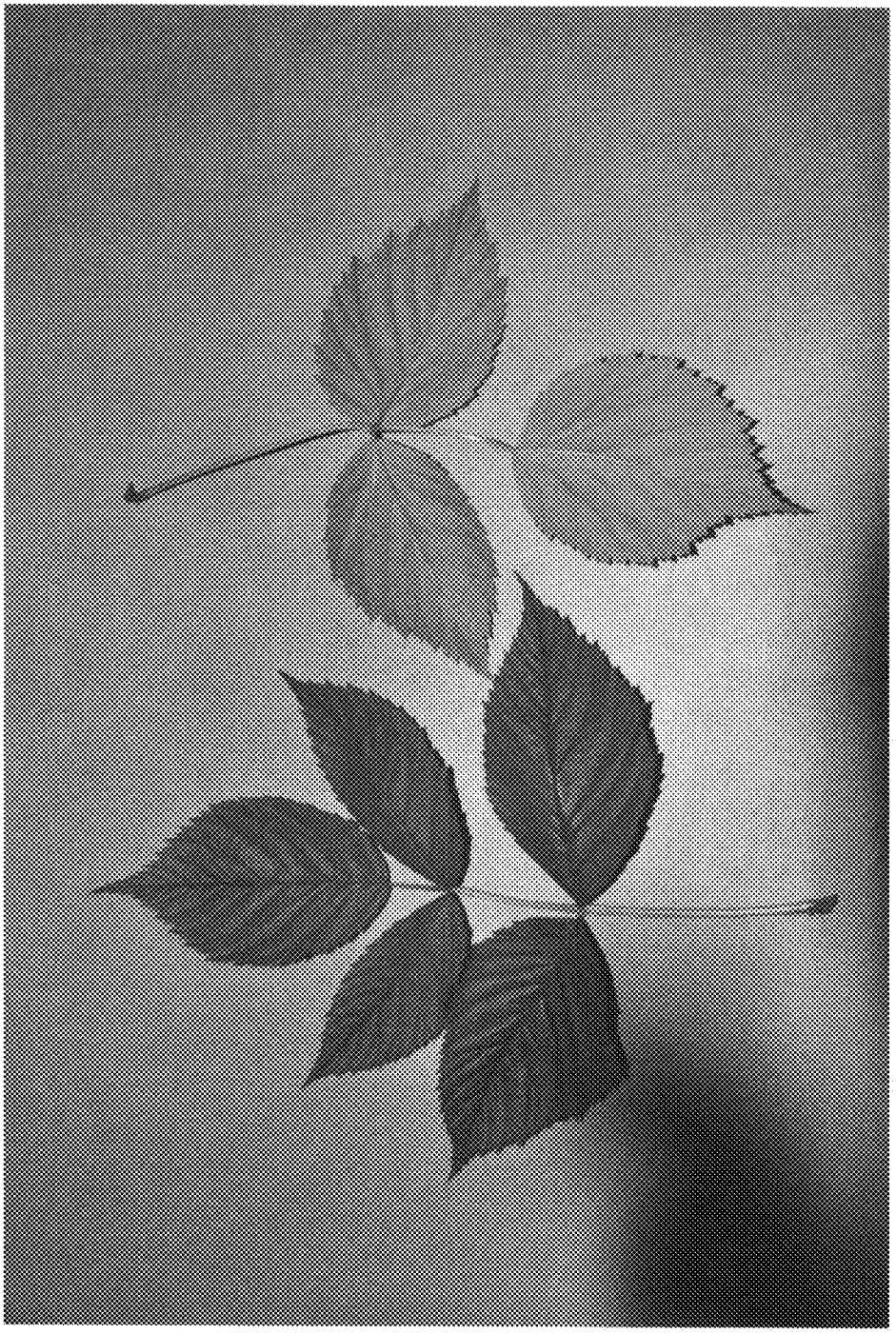
FIGS. 1A and 1B illustrate both the upper surface (FIG. 1A) and the lower surface (FIG. 1B) of plant leaves of variety 'DrisRaspTen'.

The following descriptions set forth the distinctive characteristics of 'DrisRaspTen'. The data that define these characteristics are based on observations taken in Santa Cruz County, Calif. from Year 1 to Year 7. This description is in accordance with UPOV terminology. Color designations, color descriptions, and other phenotypical descriptions may deviate from the stated values and descriptions depending upon variation in environmental, seasonal, climatic and cultural conditions. 'DrisRaspTen' has not been observed under all possible environmental conditions. The botanical description of 'DrisRaspTen' was taken from six-month-old plants. The indicated values represent averages calculated from measurements of several plants. Color references are primarily to The R.H.S. Colour Chart of The Royal Horticultural Society of London (R.H.S.) (2007 edition). Descriptive terminology follows the *Plant Identification Terminology, An illustrated Glossary,* 2nd edition by James G. Harris and Melinda Woolf Harris, unless where otherwise defined.

Classification:

*Family*.—Rosaceae.

*Botanical*.—*Rubus idaeus* L.

*Common name*.—Raspberry.

*Variety name*.—'DrisRaspTen'.

Parentage:

*Female parent*.—'Driscoll Estrella' (U.S. Plant Pat. No. 19,137).

*Male parent*.—'Driscoll Maravilla' (U.S. Plant Pat. No. 14,804).

Plant:

*Propagation*.—In vitro propagation; Tissue culture, tissue culture plant plug, and root cuttings.

*Size*.—Large.

*Height*.—180.0 cm.

*Width*.—132.0 cm.

*Length/width ratio*.—1.4.

*Productivity*.—Productivity of plants that were one-year old (primocanes) ranged from 20,000 lbs/acre per season to 30,000 lbs/acre per season; and productivity of plants that were two-years old (floricanes) ranged from 25,000 lbs/acre per season to 33,000 lbs/acre per season.

*Self-fruitfulness*.—Self-fruitful.

*New cane growth habit*.—Semi-erect or semi-upright.

Primocanes:

*Number of canes*.—2.38 per plant.

*Glaucosity (waxy bloom) on full grown shoot after picking*.—Medium.

*Cane length in autumn*.—Medium; 141.80 cm.

*Cane diameter in autumn.*—11.4 mm.
*Length of internode.*—Long.
*Internodal distance at central ⅓ of cane:* 71.1 mm.
*Length of vegetative bud.*—3.31 mm.
*Number of young shoots.*—2-5 per cane.
*Primocane color.*—RHS N144D (Strong yellow-green).
*Time of beginning of flowers on cane.*—Early June.
*Time of beginning of fruit ripening.*—Mid-July.
*Length of fruiting period.*—Mid-July through November.
*Percent of cane flowering as primocane.*—40%.
*Percent primocane yield of total yield.*—50%.
*Glaucosity (waxy bloom) on cane in autumn.*—Medium.
*Cane strength in autumn (of full grown shoot after picking).*—Medium.
*Shape of cane cross section (from mid cane of primocane).*—Rounded to angular.
*Pubescence on canes.*—Present.

Floricanes:
*Dormant cane length in summer.*—33.67 inches.
*Dormant cane diameter in summer.*—9.95 mm.
*Dormant cane color in summer.*—RHS N167B (Medium greyed-orange).
*Fruiting lateral attitude in summer.*—Semi-erect.
*Fruiting lateral length in summer.*—23.5 inches.
*Fruiting lateral diameter in summer.*—9.95 mm.
*Time of generative bud burst.*—March.
*Time of beginning of flowers.*—Late March.
*Time of beginning of fruit ripening.*—Late April.
*Length of fruiting period.*—Late April through late July.

Prickles (spines):
*Density of spines on central third.*—28.88 per area of 5 mm.
*Length of base of prickles.*—2.33 mm.
*Length of prickles (from base to tip).*—0.81 mm.
*Diameter of prickles.*—1.41 mm.
*Length at 1.0 m height at end of harvest season (from base to tip).*—1.0 mm.
*Color (pigmentation).*—RHS 166A (Dark greyed-orange).
*Attitude of tip.*—Horizontal.
*Texture.*—Fine.
*Presence and distribution on petioles.*—Absent.

Leaves (FIG. 1):
*Terminal leaflet.*—Length: Medium; 12.1 cm. Width: Medium; 7.9 cm. Length/width ratio: 1.5. Leaf color: Green color of upper surface: RHS 138A (Medium green). Green color of lower surface: RHS 191B (Medium greyed-green). Profile in cross section: Flat (straight). Relief between the veins (Rugosity): Medium. Overlapping or relative position of lateral leaflets: Free. Glossiness: Medium. Shape: Ovate. Apex.: Acuminate. Base: Obtuse. Margin: Crenate. Arrangement (orientation): Simple.
*Lateral leaflets (basal pair).*—Number of leaflets: Sometimes 3 and sometimes 5. Size: Length: 108.6 mm. Width: 78.5 mm. Length/width ratio: 1.4. Arrangement (orientation): Opposite (2 leaves per node). Shape: Ovate. Apex: Acuminate. Base: Obtuse. Margin: Doubly serrate. Lateral leaflet length to stalklet (lower pair): Long.
*Rachis length between terminal leaflet and adjacent lateral leaflets.*—35.6 mm.
*Rachis diameter.*—1.76 mm.
*Petiole.*—Length: 3.3 mm. Diameter: 1.35 mm. Pigmentation of upper surface: RHS 144B (Medium yellow-green). Pigmentation of underside: RHS 144D (Light yellow-green).

Stipules:
*Orientation.*—Reflexed.
*Number.*—150-300 per plant.
*Shape.*—Narrow elongated.
*Length.*—7 mm.
*Width.*—0.34 mm.
*Color of upper surface.*—RHS 143C (Strong yellow-green)
*Color of lower surface.*—RHS 143B (Strong yellow-green).

Figure 2:
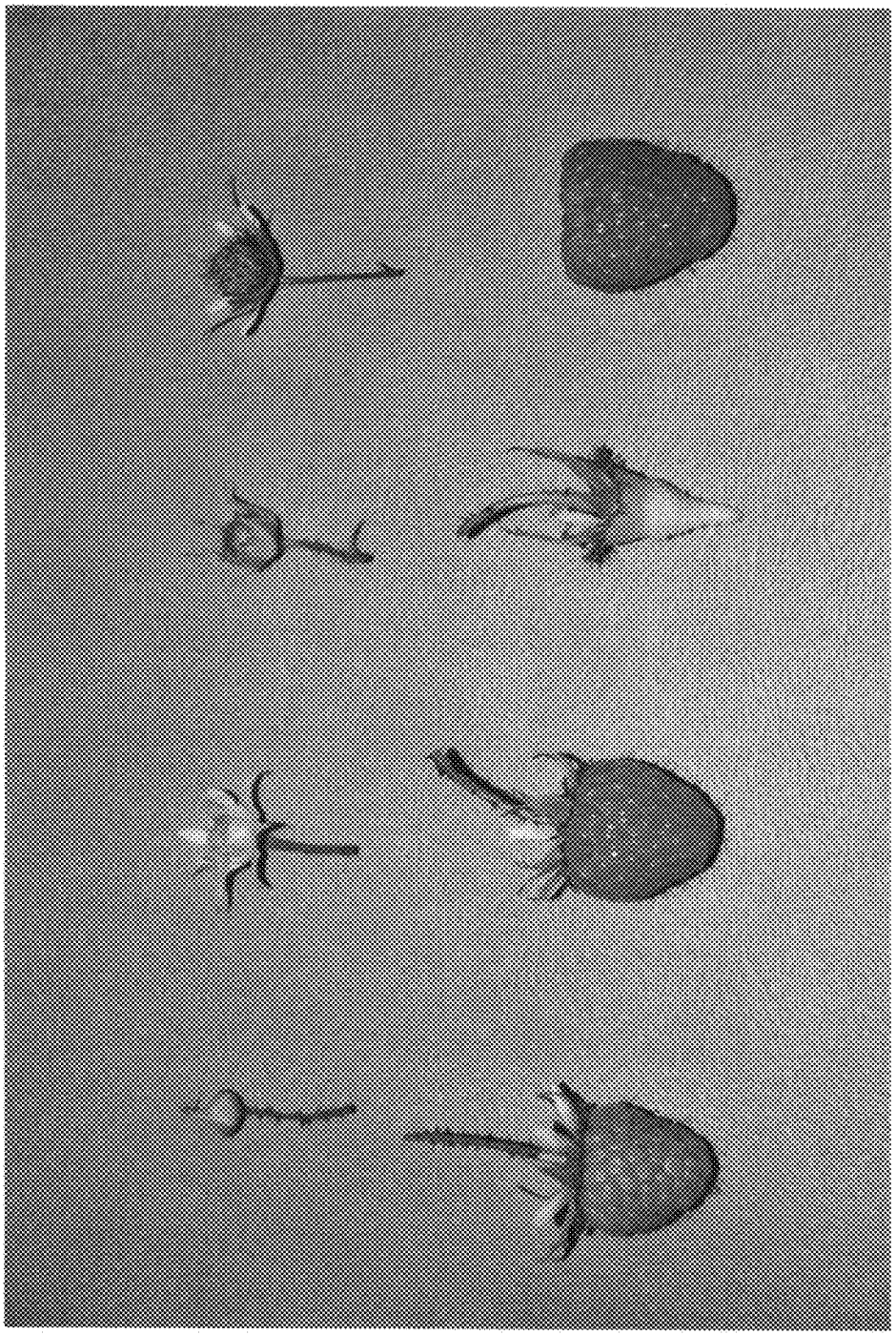
FIG. 2 illustrates typical flowers and fruit of variety 'DrisRaspTen' at various stages of development.

Flowers (FIG. 2):
*Size.*—Medium.
*Diameter.*—17.10 mm.
*Petal length.*—8.29 mm.
*Petal width.*—3.06 mm.
*Length/width ratio.*—2.7.
*Petal color.*—RHS 155C.
*Flower bud.*—Color: RHS 139C (Moderate yellow-green). Length: 1.0 cm. Width: 0.7 cm.
*Flowering period.*—Primocane: Early June through late September. Floricane: Late March through late June.
*Pedicel.*—Number of spines: 37.38. Anthocyanin coloration: Absent. Color: RHS 139C (Moderate yellow-green). Length: Medium; 25.41 mm. Diameter: 0.80 mm.
*Sepal.*—Color: RHS 139C (Moderate yellow-green). Length: 1.6 cm. Width: 0.6 cm.

Peduncle:
*Length.*—8.6 inches.
*Diameter at base.*—5.3 mm.
*Anthocyanin coloration.*—Absent.
*Intensity of anthocyanin coloration.*—Absent or very weak.
*Color.*—RHS 139C (Moderate yellow-green).

Fruit (FIG. 2):
*Length.*—Long; 26.23 mm.
*Diameter.*—Medium; 22.55 mm.
*Ratio of length to width.*—1.2.
*Average number of drupelets per fruit.*—77.
*Weight (g/fruit).*—Primocane: 5.2 g/fruit. Floricane: 5.1 g/fruit.
*Soluble solids (in brix).*—9.84%.
*Titratable acidity (as citric acid).*—8.5%.
*Weight of seeds.*—0.001545 g/seed.
*Size.*—Medium.
*Shape.*—Ovate (broad conical).
*Length of single drupelet.*—3.23 mm.
*Diameter of single drupelet.*—2.16 mm.
*Color.*—Immature fruit: RHS 143D (Light green). Maturing fruit: RHS 11B (Medium yellow). Mature fruit color: RHS 34B (Medium orange-red).
*Glossiness.*—Strong.
*Firmness.*—Medium.
*Adherence to plug.*—Easy.
*Main bearing type.*—Both on previous year's cane in summer and on current year's cane in autumn.

*Time of ripening*.—Primocane: Late (Mid-July through November). Floricane: Medium (Late April through late July).

*Harvest season*.—Primocane: Mid-July to November. Floricane: Late April to late July.

*Yield*.—Yield of plants that were one-year old (primocanes) ranged from 20,000 lbs/acre per season to 30,000 lbs/acre per season; and yield of plants that were two-years old (floricanes) ranged from 25,000 lbs/acre per season to 33,000 lbs/acre per season.

COMPARISONS TO COMMERCIAL RASPBERRY VARIETIES

'DrisRaspTen' differs from the proprietary female parent 'Driscoll Estrella' (U.S. Plant Pat. No. 19,137) in that 'DrisRaspTen' produces fruit having a multicolor phenotype, whereas 'Driscoll Estrella' does not produce multicolored fruit. Further, 'DrisRaspTen' has a lower number of young shoots than 'Driscoll Estrella'. Further, anthocyanin pigmentation is present in the canes and prickles of 'DrisRaspTen', whereas anthocyanin pigmentation is absent in the canes and prickles of 'Driscoll Estrella'. Further, 'DrisRaspTen' has less firm fruit than 'Driscoll Estrella'. Additionally, 'DrisRaspTen' has a larger fruit size and a larger plant size as compared to 'Driscoll Estrella'.

'DrisRaspTen' differs from the proprietary male parent 'Driscoll Maravilla' (U.S. Plant Pat. No. 14,804) in that 'DrisRaspTen' produces fruit having a multicolor phenotype, whereas 'Driscoll Maravilla' does not produce multicolored fruit. Further, 'DrisRaspTen' has easier fruit adherence to the plug than does 'Driscoll Maravilla'. Moreover, 'DrisRaspTen' has a lower number of young shoots, larger fruit size, smaller seed weight, and higher length/width ratio as compared to 'Driscoll Maravilla'.

What is claimed is:

1. A new and distinct variety of raspberry plant designated 'DrisRaspTen' as shown and described herein.

* * * * *